(12) United States Patent  (10) Patent No.: US 8,806,922 B2
Hochgraeber  (45) Date of Patent: Aug. 19, 2014

(54) SAMPLE INJECTOR FOR LIQUID CHROMATOGRAPHY, PARTICULARLY FOR HIGH PERFORMANCE LIQUID CHROMATOGRAPHY

(75) Inventor: Hermann Hochgraeber, Offenberg-Neuhausen (DE)

(73) Assignee: Dionex Softron GmbH, Germering (DE)

( * ) Notice: Subject to any disclaimer, the term of this patent is extended or adjusted under 35 U.S.C. 154(b) by 769 days.

(21) Appl. No.: 12/863,976

(22) PCT Filed: Jan. 7, 2009

(86) PCT No.: PCT/DE2009/000004
§ 371 (c)(1),
(2), (4) Date: Jul. 21, 2010

(87) PCT Pub. No.: WO2009/092345
PCT Pub. Date: Jul. 30, 2009

(65) Prior Publication Data
US 2010/0288025 A1  Nov. 18, 2010

(30) Foreign Application Priority Data
Jan. 25, 2008 (DE) .......................... 10 2008 006 266

(51) Int. Cl.
*G01N 13/00* (2006.01)
*G01N 30/24* (2006.01)

(52) U.S. Cl.
CPC ...................................... *G01N 30/24* (2013.01)
USPC .......................................................... 73/61.55

(58) Field of Classification Search
CPC ................................ G01N 30/24; G01N 30/16
USPC ............................... 73/61.52, 61.55
See application file for complete search history.

(56) References Cited

U.S. PATENT DOCUMENTS 3,530,721 A  9/1970  Hrdina
4,300,393 A * 11/1981  Stearns ...................... 73/863.11
(Continued)

FOREIGN PATENT DOCUMENTS

WO  WO 2006/083776 A2  8/2006
WO    2007/109529 A2  9/2007
WO  WO 2008/005845 A2  1/2008

OTHER PUBLICATIONS

E.M. Fujinari, "New Alternative to Normal Phase HPLC Automation Using Methylene Chloride Mobile Phases: A Synchronized Dual Switching Valve Loop Injection System," Journal of High Resolution Chromatography & Chromatography Communications, Aug. 1988, pp. 595-598, No. 8, Heidelberg, W. Germany (4 pages).

*Primary Examiner* — Hezron E Williams
*Assistant Examiner* — Rodney T Frank
(74) *Attorney, Agent, or Firm* — The Culbertson Group, P.C.

(57) ABSTRACT

A sample injector for liquid chromatography includes an injection valve having a waste port, two sample loop ports, and two high-pressure ports. One high-pressure port can be connected to a pump and the other high-pressure port can be connected to a chromatography column. A sample loop is connected to one of the sample loop ports on one end and to a pump volume of a sample conveying device on the other end. A section of the sample loop can be separated to facilitate receiving a sample fluid in the sample loop. A control unit controls the injection valve and the sample conveying device. The sample injector allows a sample to be loaded into the sample loop and then pressurized to an operating pressure prior to injecting the sample into the chromatography column. The sample loop may also be isolated from the operating pressure for facilitating depressurization of the loop.

15 Claims, 9 Drawing Sheets

(56) References Cited

U.S. PATENT DOCUMENTS

| | | | |
|---|---|---|---|
| 4,444,066 A * | 4/1984 | Ogle et al. | 73/863.72 |
| 4,939,943 A | 7/1990 | Strohmeier | |
| 5,207,109 A * | 5/1993 | Olsen | 73/863.73 |
| 5,637,208 A | 6/1997 | Dourdeville | |
| 6,012,487 A * | 1/2000 | Hauck | 137/625.11 |
| 6,155,123 A * | 12/2000 | Bakalyar | 73/864.83 |
| 6,260,407 B1 * | 7/2001 | Petro et al. | 73/61.52 |
| 6,281,019 B1 | 8/2001 | Werringloer | |
| 6,382,035 B1 * | 5/2002 | Nichols | 73/863.72 |
| 6,416,663 B1 * | 7/2002 | Miroslav et al. | 210/198.2 |
| 6,475,391 B2 * | 11/2002 | Safir et al. | 506/12 |
| 6,874,354 B2 * | 4/2005 | Cueni et al. | 73/61.55 |
| 6,976,383 B2 * | 12/2005 | Petro et al. | 73/61.55 |
| 7,503,203 B2 * | 3/2009 | Gamache et al. | 73/23.42 |
| 2009/0145205 A1 | 6/2009 | Hochgraeber et al. | |

* cited by examiner

SAMPLE INJECTOR FOR LIQUID CHROMATOGRAPHY, PARTICULARLY FOR HIGH PERFORMANCE LIQUID CHROMATOGRAPHY

TECHNICAL FIELD OF THE INVENTION

The invention pertains to a sample injector for liquid chromatography, particularly for high performance liquid chromatography (HPLC). The sample injector provides for pressure compensation during a sample injection sequence, or during a post sample injection sequence, or during both sequences.

BACKGROUND OF THE INVENTION

In HPLC, a sample to be examined needs to be injected into a high-pressure fluid flow, wherein this flow can be interrupted only as briefly as possible. For this purpose, high-pressure injection valves are used that allow a nearly uninterrupted change-over of the fluid flow. Such a design is described, for example, in U.S. Pat. No. 3,530,721. This patent was derived from an original application that was published in 1965.

U.S. Pat. No. 4,939,943 discloses a sample injector with a "high pressure syringe unit." The basic Split Loop Principle of the sample injector disclosed in this application has proven effective in HPLC.

Furthermore, WO 2006/083776 discloses a sample injector for preventing pressure surges that occur during the actuation of the high-pressure valve and could negatively affect the efficiency and the service life of the chromatography column.

During the actuation of the injection valve, compression and decompression volumes flow through the valve with high speeds. According to non-previously-published German Patent Application DE 10 2007 059 651 A1 of the applicant of Dec. 10, 2007, which pertains to a sample injector for high performance liquid chromatography and features a high-pressure change-over valve with optimized service life, these flows cause damage to the high-pressure valve components.

The service life of the high-pressure change-over valve determines the operating costs of an HPLC system. These costs should be maintained as low as possible by minimizing the wear of the high-pressure valve components.

SUMMARY OF THE INVENTION

The invention includes a sample injector for liquid chromatography, particularly for high performance liquid chromatography, in which the injection valve also has an improved service life under extremely high pressures.

Embodiments of the invention apply the Split Loop Principle for a sample injector to facilitate a pressure compensation when the switching positions of the injection valve are changed. The pressure compensation is made possible by an injection valve which features a PRESSURE COMPENSATION position, in which the sample loop ports of the injection valve connected to the ends of the sample loop are not connected to other ports in the injection valve.

In the Split Loop Principle, the sample loop is divided in the connecting piece between the sample conveying device that may be realized, for example, in the form of a syringe and the respective sample loop port of the injection valve. In order to take in the required sample volume or to take in a flushing medium, the end of the intake segment of the separated connecting piece of the sample loop that is connected to the sample conveying device is moved to a sample container or a container for a flushing medium. Subsequently, the divided connecting piece of the sample loop is reconnected such that the sample volume can be injected into the chromatography column by means of the pump in the INJECT position of the injection valve. This basic principle is already described in U.S. Pat. No. 4,939,943. In this case, the special Split Loop Principle provides the advantage that the sample conveying device is flushed with eluent after the injection of the sample such that it is normally not required to flush the sample conveying device, the sample loop and the injection valve after the injection of a sample.

After taking in the sample volume in the LOAD position, the injection valve is, according to one or more embodiments of the invention, changed over into the PRESSURE COMPENSATION position, in which the sample loop ports are shut in a pressure-tight fashion. In this position, the drive of the sample conveying device is controlled in such a way that pressure builds up in the closed sample loop and in the pump volume of the sample conveying device, wherein this pressure essentially corresponds to the pressure, with which the pump feeds the fluid to the chromatography column in the LOAD position or in the INJECT position. Even if the pressure in the sample loop is not identical to the pressure of the pump before the injection valve is changed over from the PRESSURE COMPENSATION position into the INJECT position and a slight differential pressure remains, this slight differential pressure is, according to the invention, maintained so low that it can neither disadvantageously effect the flow through the chromatography column nor cause damage to the injection valve or the chromatography column.

This applies analogously to the change-over from the INJECT position into the LOAD position. In this case, the valve also is initially changed over from the INJECT position into the PRESSURE COMPENSATION position, in which the pressure that essentially corresponds to the pump pressure is reduced until essentially the ambient pressure is reached. If applicable, a slight, harmless differential pressure may also remain in this case when the valve is changed over from the PRESSURE COMPENSATION into the LOAD position.

According to the invention, the pressure compensation (pressure increase or pressure reduction) in the sample loop is achieved by controlling the drive of the sample conveying device accordingly.

In contrast to prior sample injectors, the fluid flows created during the pressure compensation no longer flow through the change-over valve such that damage to valve components due to excessively high flow speeds can no longer occur.

Naturally, this objective also is at least partially attained if the pressure compensation is only carried out in one of the two change-over directions described above.

According to one preferred embodiment of the invention, the two high-pressure ports are connected in the PRESSURE COMPENSATION position of the injection valve. Due to this measure, the flow of the fluid through the chromatography column is maintained and no undesirable peaks can occur in the progression of pressure during the change-over processes.

According to one embodiment of the invention, the injection valve features a rotor and a stator, wherein the rotor features a face that cooperates with the face of the stator and contains at least three grooves that either connect or shut port opening cross sections of the high-pressure ports, the sample loop ports and the waste port arranged in the face of the stator in a pressure-tight fashion as a function of the rotational position of the rotor relative to the stator. The groove that connects the two high-pressure ports in the LOAD position of the injection valve is realized so long that it still connects the high-pressure ports after the stator and the rotor are turned into the PRESSURE COMPENSATION position. This groove therefore is elongated in comparison with the corresponding groove of conventional injection valves.

According to the preferred field of application of the invention, namely in HPLC, the sample conveying device is realized in a high-pressure-resistant fashion and can generate the pressures used in HPLC, preferably pressures greater than 500-600 bar, particularly pressures greater than 1000 bar.

The sample conveying device may feature a movable element that is guided in a pump volume in a sealed fashion and can be moved by means of a drive of the sample conveying device that is controlled by the control unit in order to convey the fluid contained in the pump volume. The sample conveying device may, in particular, be realized in the form of a syringe that is driven by means of a drive, wherein the movable element is formed by the plunger of the syringe.

The control unit can move the plunger or the movable element by a predetermined distance after the PRESSURE COMPENSATION position of the injection valve is reached by controlling the drive accordingly, wherein this predetermined distance suffices for realizing a change of the pump volume of the sample conveying device required due to the elasticities of the devices conveying the fluid and the compressibility of the fluid itself such that a pressure reduction in the sample loop to essentially the ambient pressure can be achieved by increasing the pump volume and a pressure increase in the sample loop to essentially the operating pressure of the pump can be achieved by decreasing the pump volume. The movement of the movable element may take place in a controlled or regulated fashion.

In order to allow a control of the pressure or the ultimate pressure during the pressure compensation in the sample loop, a sensor may be provided that measures the pressure of the fluid in the closed sample loop or in the pump volume of the sample conveying device at least while the injection valve is in the PRESSURE COMPENSATION position.

In this variation, the signal of the pressure sensor is preferably fed to the control unit, wherein the control unit compares the pressure of the fluid with a nominal pressure value and controls the sample conveying device in such a way that the pressure of the fluid reaches a nominal high-pressure value before the injection valve is changed over from the PRESSURE COMPENSATION position into the INJECT position and/or that the pressure of the fluid reaches a nominal low-pressure value before the injection valve is changed over from the PRESSURE COMPENSATION position into the LOAD position.

These and other advantages and features of the invention will be apparent from the following description of the preferred embodiments, considered along with the accompanying drawings.

BRIEF DESCRIPTION OF THE DRAWINGS

The invention is described in greater detail below with reference to the drawings. In these drawings.

DESCRIPTION OF ILLUSTRATIVE EMBODIMENTS

Figure 1:
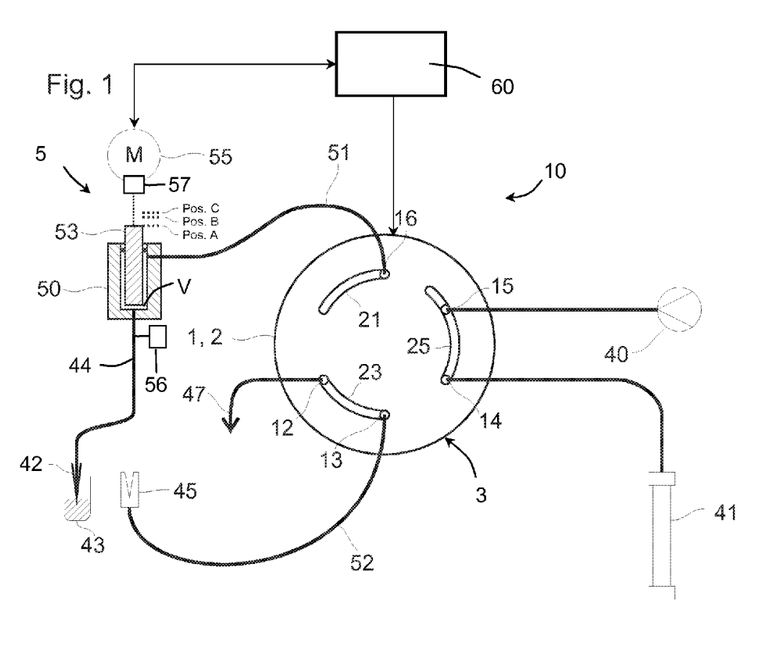
FIG. 1 shows a schematic representation of an HPLC system with a sample injector according to the invention, to which a chromatography column is connected, wherein the injection valve is situated in the LOAD position and the process of taking in a sample volume can begin in the state shown.

FIG. 1 shows a schematic representation of an HPLC system with a sample injector 10 that operates in accordance with the Split Loop Principle and features a sample conveying device 5, an injection valve 3 and a high-pressure pump 40. The sample injector 10 furthermore features a sample loop that includes a first connecting piece 51 and a second connecting piece 52, 44. These may be comprised of a pressure-resistant line with a small diameter, for example in the form of a capillary tube of glass or stainless steel. The connecting piece 51 is connected to a first sample loop port 16 of the injection valve 3 and to the sample conveying device or its pump volume V, respectively. The second connecting piece is comprised of an intake segment 44 and a feed segment 52 and is realized in a separable fashion. For this purpose, the feed segment 52 leads into an injection port 45 that is connected to a second sample loop port 13 of the injection valve 3 via the feed segment 52. The intake segment 44 that is connected to the pump volume V of the sample conveying device 5 with one end features on its other end a sample needle 42, by means of which the intake segment 44 can be connected to the injection port 45.

However, the sample needle 42 can also be moved to a sample container 43 and take in a defined sample volume into the intake segment 44 as described in greater detail below. Furthermore, the sample needle 41 can also be moved to a (not-shown) container for a flushing fluid in order to withdraw flushing fluid for a flushing process and to clean the sample loop 51, 52, 44, the pump volume V and, if applicable, also the ports and the grooves or channels of the injection valve. Due to the special topology of the Split Loop Principle shown, flushing of the sample loop 51, 52, 44 and of the sample conveying device 5 is normally not required because they are flushed during an injection process anyway, namely with eluent supplied by the pump 40. However, the outside of the sample needle 42 can also be cleaned by immersing the needle into a container with cleaning or flushing fluid.

In the embodiment shown, the sample conveying device 5 comprises a syringe 50, in which a plunger 53 is guided in a displaceable and pressure-tight fashion. The plunger 53 is driven by means of a drive 55 that is realized, for example, in the form of a stepping motor. The drive 55 is controlled by a control unit 60. The control unit 60 also controls the changeover processes of the injection valve 3 that features a not-shown controllable drive.

A waste port 12 of the injection valve is connected to a waste line 47, from which fluid can be discharged into a not-shown waste reservoir.

The high-pressure pump 40 is connected to a high-pressure port 15 of the injection valve. A chromatography column 41 is connected to the other high-pressure port 14. The high-pressure pump 40 may be integrated into and form part of the sample injector or be arranged in another unit or a separate pump unit.

The injection valve 3 includes a stator 1 and a rotor 2. The stator 1 features the two high-pressure ports 14, 15, the two sample loop ports 13, 16 and the waste port 12. The injection valve 3 is connected to the other functional elements of the HPLC system via these ports and the above-described connecting lines that may be realized in the form of capillary connections. The high-pressure screw connections required for this purpose are not illustrated in FIG. 1 in order to provide a better overview. For reasons of simplicity, the injection valve is illustrated in the interface between the stator 1 and the rotor 2, wherein the design of the face of the stator 1 and the design of the face of the rotor 2 are shown in order to better comprehend the function of the injection valve. Within the injection valve 3, the ports are realized in the form of bores that lead to the other side of the stator 1. The rotor 2 features a number of arc-shaped grooves 21, 23, 25 that are exactly aligned with the bores of the input and output ports.

The rotor 2 is pressed against the stator with a certain pressing force such that a common interface between the rotor 1 and the stator 2 is formed, at which both components are mutually sealed. In this case, the pressing force is chosen so high that the arrangement also remains sealed at the highest pressures to be expected.

In the first LOAD position of the valve 3 illustrated in FIG. 1, the grooves 21, 23, 25 are aligned relative to the ports 12-16 in such a way that the grooves 23 and 25 respectively connect the two high-pressure ports 14, 15 and the waste port 12 to the sample loop port 13. In this LOAD position, the high-pressure pump 40 therefore conveys fluid in the direction of the chromatography column 41. Furthermore, the sample loop port 16 is closed in a pressure-tight fashion.

Figure 2:
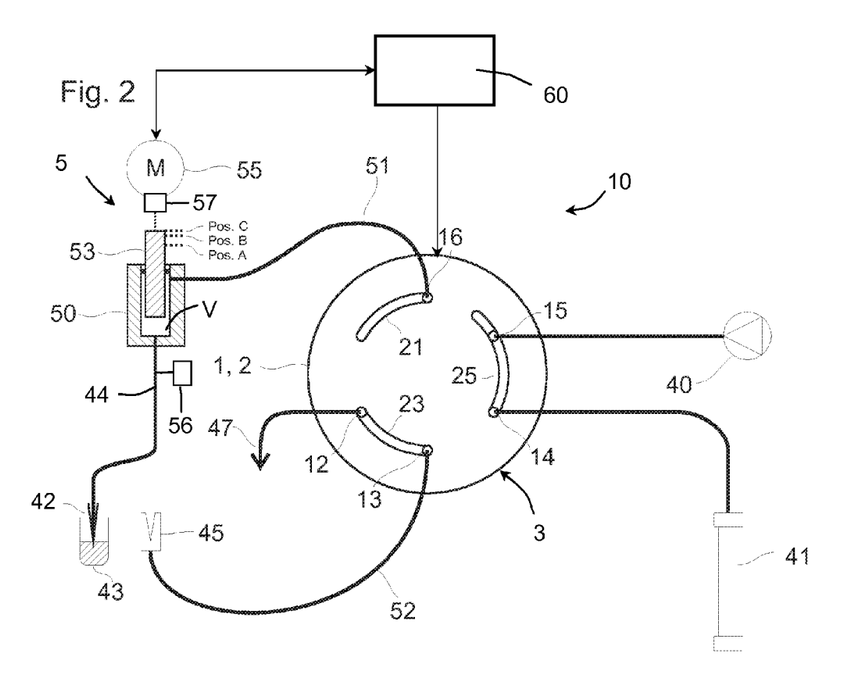
FIG. 2 shows the HPLC system of FIG. 1, wherein the plunger of the syringe was moved into the end position (position C) in order to take in the sample volume.

In the state illustrated in FIG. 1, the sample needle 42 is moved into the sample container 43 such that a sample volume can be taken in. For this purpose, the plunger 53 is situated in the position A and can be moved into the position C by the control unit 60 in order to take in the sample volume. The desired defined sample volume is then withdrawn into the intake segment 44, wherein the volume of the sample is smaller than the volume of the intake segment 44 such that the sample fluid cannot mix with the fluid supplied by the high-pressure pump in the pump volume. FIG. 2 shows the state of the HPLC system after the intake process is completed.

Figure 3:
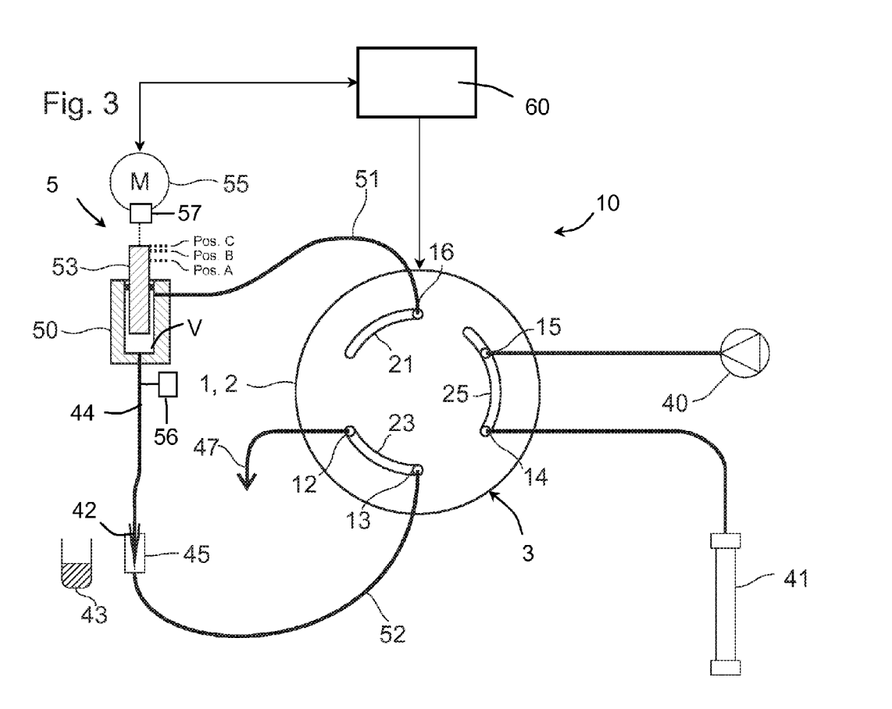
FIG. 3 shows the HPLC system of FIG. 2, wherein the sample needle was moved into the injection port.

In order to inject the sample volume situated in the intake segment 44, the sample needle 42 is moved into the injection port 45. This port seals the needle point in a high-pressure-resistant fashion. This state is illustrated in FIG. 3.

Figure 4:
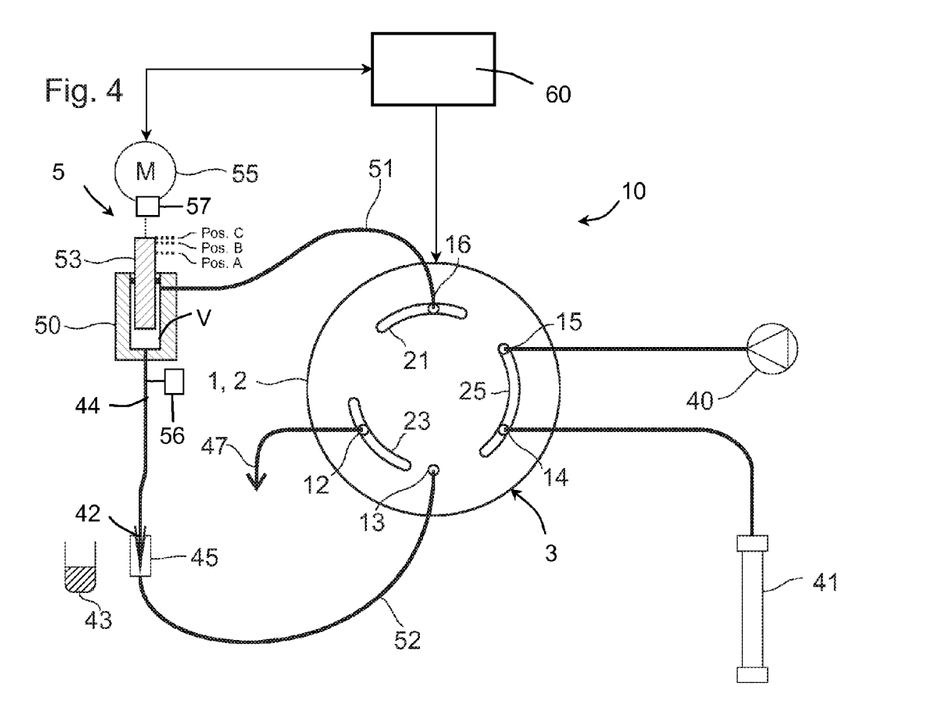
FIG. 4 shows the HPLC system of FIG. 3, wherein the injection valve was changed over from the LOAD position into the PRESSURE COMPENSATION position.

In the next step, the pressure in the sample loop is adjusted to the operating pressure of the chromatography column 41, i.e., to the pressure, with which the high-pressure pump 40 supplies fluid to the inlet of the chromatography column 41. For this purpose, the injection valve is initially changed over into a PRESSURE COMPENSATION position, in which the connecting piece 51 and the second connecting piece or the feed segment 52 of the sample loop are not connected to the other components connected to the injection valve 3 (FIG. 4).

Figure 5:
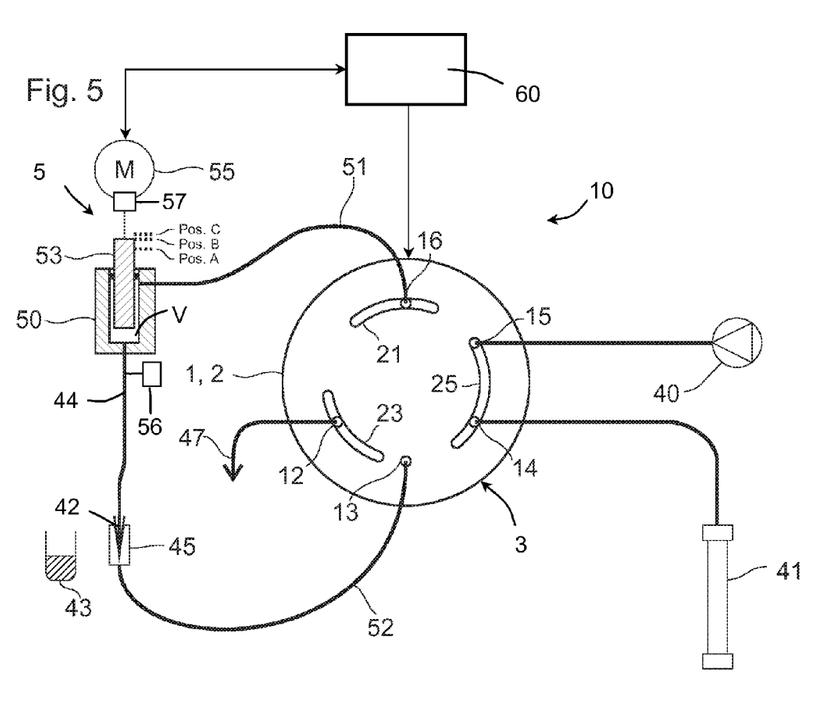
FIG. 5 shows the HPLC system of FIG. 4, wherein the plunger was moved into the position B in order to realize a pressure compensation (pressure increase) in the sample loop.
Figure 6:
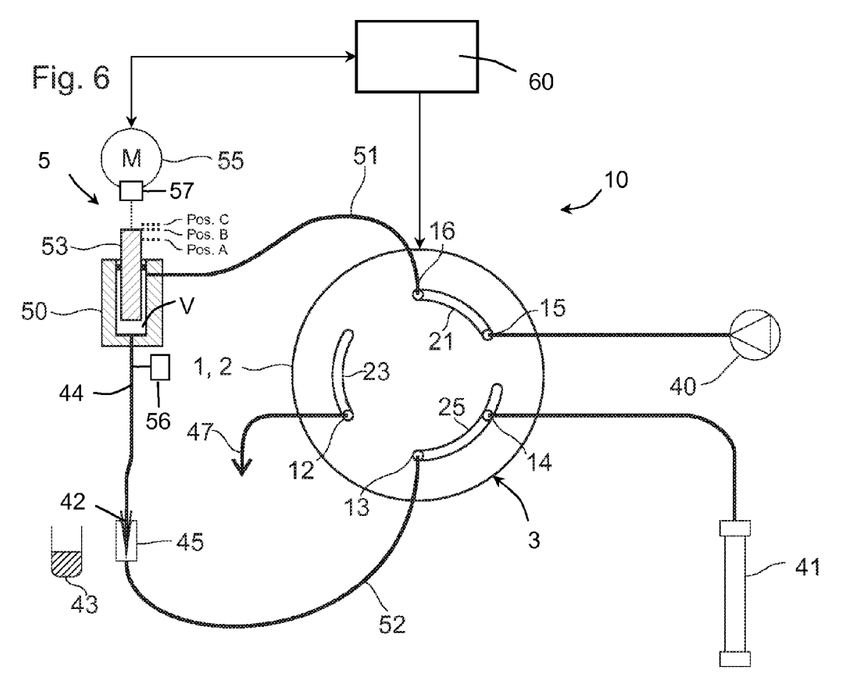
FIG. 6 shows the HPLC system of FIG. 5, wherein the injection valve was changed over from the PRESSURE COMPENSATION position into the INJECT position.

In this PRESSURE COMPENSATION position, the plunger 53 of the high-pressure-resistant sample conveying device is moved into the position B (FIG. 5). In order to prevent an interruption of the flow through the chromatography column 41 while conveying the volume required for the compression of the sample loop content, the groove 25 in the rotor 2 of the valve is realized in a correspondingly elongated fashion such that the two high-pressure ports 14, 15 are still connected in the PRESSURE COMPENSATION position. The travel of the plunger 53 from position C into position B required for building up the pressure can be calculated from the compressibility of the fluid volume enclosed in the sample conveying device 5 and in the sample loop, the elasticity of the arrangement and the current pump pressure. Alternatively, a pressure compensation can be achieved with the aid of a control circuit for the pressure in the high-pressure-resistant sample conveying device. For this purpose, the pressure needs to be measured at a suitable location and the position of the plunger 53 in the sample conveying device 5 needs to be adjusted by the drive 55 in such a way that the pressure corresponds to the required target pressure (=column pressure). Pressure measurement may be realized with a pressure sensor such as sensor 56 or indirectly by means of a force measurement. Conceivable solutions are force measurements on the plunger 53 or in the drive 55. After pressure equality is achieved, the valve is changed over into the INJECT position in order to inject the sample volume into the column 41 (FIG. 6).

In the embodiment shown, the control unit 60 measures the force that the drive 55 needs to exert in order to achieve a corresponding compression in the sample loop. For this purpose, the drive 55 may feature an integrated sensor 57, the signal of which is fed to the control unit 60 (as indicated with a double arrow between the drive 55 and the control unit 60). Due to this measure, the control unit can determine the actual pressure in the pump volume and therefore in the sample loop (the pressure drop in the connecting pieces and in the valve is negligibly small) and adjust this pressure to the desired value.

Figure 7:
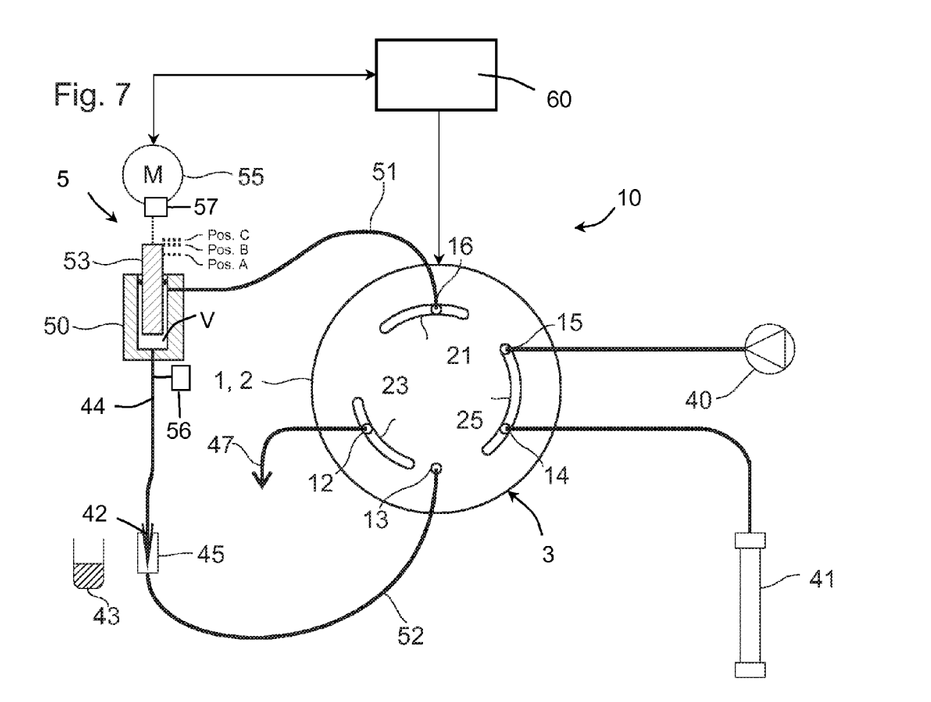
FIG. 7 shows the HPLC system of FIG. 6, wherein the injection valve was changed over from the INJECT position into the PRESSURE COMPENSATION position after the injection of the sample volume.

After the entire sample volume has been conveyed from the intake segment 44 to the column 41 by means of the fluid conveyed by the pump 40, the valve can be once again changed over into the PRESSURE COMPENSATION position in order to decompress the sample loop (FIG. 7).

Figure 8:
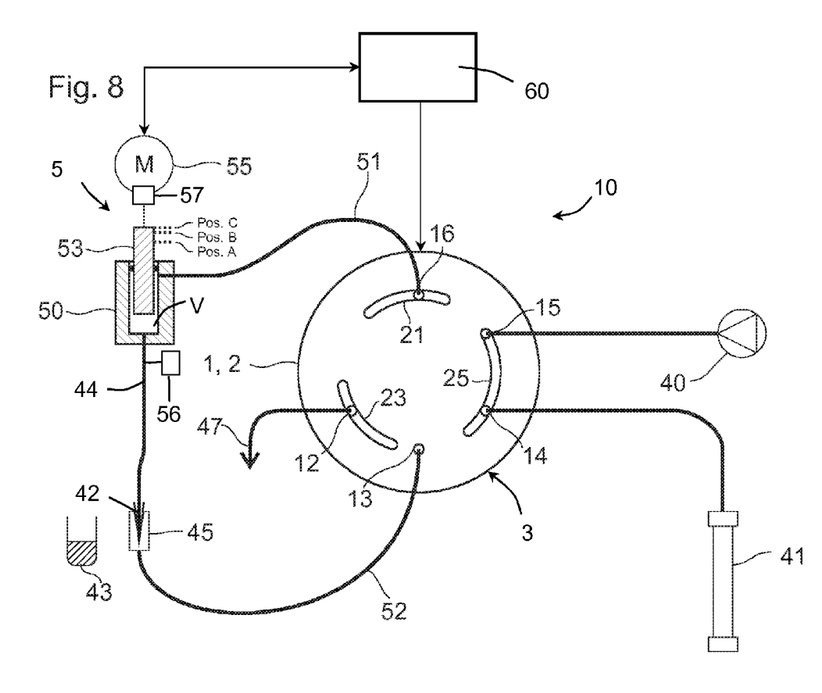
FIG. 8 shows the HPLC system of FIG. 7, wherein the plunger was moved into the end position (position C) in order to realize a pressure compensation (pressure reduction)

The plunger 53 is moved from the position illustrated in FIG. 7 into position C. This causes the pressure in the sample loop to be adjusted to the atmospheric pressure. This state of the HPLC system is illustrated in FIG. 8. During this decompression time in the PRESSURE COMPENSATION position of the injection valve 3, the column 41 is already connected to the pump 40 via the elongated groove 25 in order to prevent pressure drops. The travel of the plunger 53 from position B to position C can either be calculated analogous to the compression in FIG. 5 or determined by measuring and controlling the pressure. Alternatively, the pressure can also be determined indirectly by means of a force measurement on the plunger 53 or on the drive 55 of the plunger.

Figure 9:
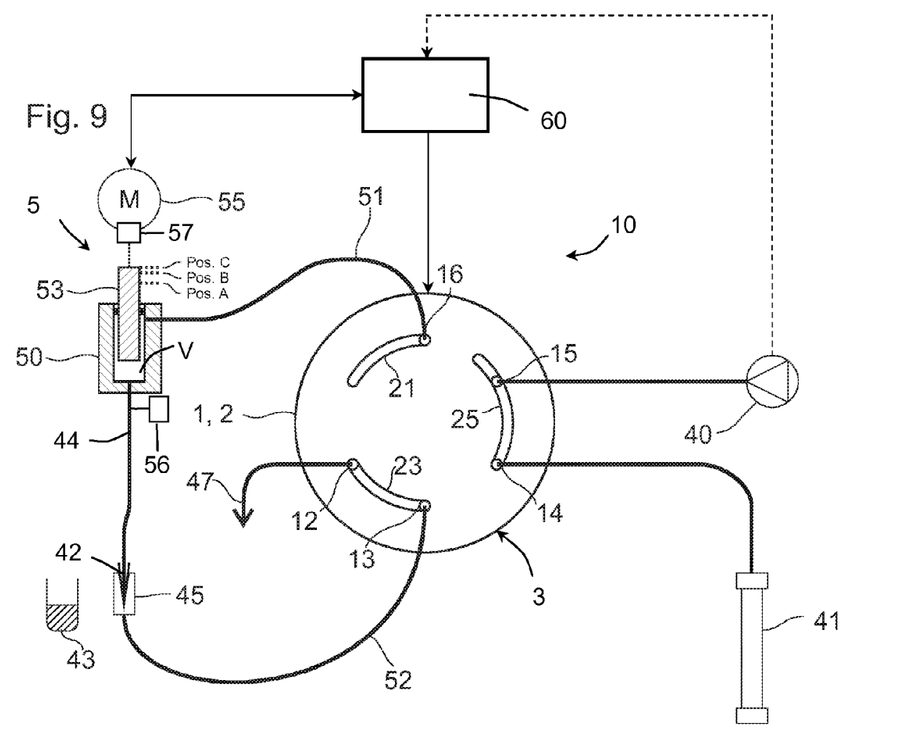
FIG. 9 shows the HPLC system of FIG. 8, wherein the injection valve was changed over from the PRESSURE COMPENSATION position into the LOAD position.

After the sample loop has been decompressed, the valve 3 is changed over into the LOAD position (FIG. 9). No damaging flows in the injection valve occur during this process.

The plunger 53 of the high-pressure-resistant sample conveying device 5 can now be moved back into the starting position A. The excess quantity of fluid is discharged via the waste connection 47. The unpressurized needle 42 can subsequently be moved from the needle seat of the injection port 45 to the corresponding sample bottle in order to take in the next sample.

The position C during the decompression may also differ from the starting position A prior to the compression. For example, if gradients (time-controlled mixing ratio of the eluent) are pumped through the column, the position C at the end of the decompression may differ because the compressibility of the loop content may have changed.

The control unit 60 can store predetermined positions A, B, C and/or differences in the distance between these positions as a function of parameters of the entire sample injector, particularly the compressibility of the eluent, elasticity properties of the sample loop and the sample conveying device, etc. The plunger can then be automatically moved into these positions (i.e., without a control) or these positions may serve as approximate values or initial values for a controlled movement.

In order to determine the positions A, B, C and the respective travel of the plunger, a change-over of the injection valve 3 may be carried out without compression or decompression, respectively. The pressure drop can then be determined by means of a pressure sensor and the required travel as well as the respective positions B or C can be determined based on this pressure drop. The thusly determined values can then be stored and used for other change-over processes, in which a compression or decompression takes place. A corresponding sensor may also be provided in the pump 40. Pumps of this type for HPLC always feature a pressure sensor for controlling the conveyed eluent anyway. The compressibility of the medium, particularly of the eluent, can also be determined by means of the pump 40. Such pumps are realized, for example, in the form of dual-plunger pumps, in which the change-over from one plunger to the other plunger is suitably controlled or regulated by means of a pressure sensor and a control unit in such a way that a highly constant flow rate is achieved. Since the compressibility of the medium also needs to be taken into account during this change-over process, the compressibility can be determined by suitably controlling the dual-plunger pump during the change-over from one plunger to the other plunger and fed to the control unit 60 as information. This connection between the pump 40 and the control unit 60 is merely illustrated with broken lines in FIG. 9.

In the automatic sample injector shown, it is therefore ensured that the pressure in the sample loop is adjusted to the current operating pressure of the chromatography column by means of decompression in the sufficiently (high) pressure-resistant sample conveying device when the injection valve is in a special intermediate position, namely the PRESSURE COMPENSATION position, before the intake segment is moved into the flow path toward the chromatography column, i.e., before the injection valve is changed over into the INJECT position.

In addition, the pressure in the sample loop is adjusted to the atmospheric pressure (decompression) in the same intermediate position of the injection valve, namely the PRESSURE COMPENSATION position, by taking in an exactly defined additional fluid quantity into the sample conveying device before the sample loop is separated in order to take in a sample volume from a sample container, i.e., before the injection valve is changed over into the LOAD position.

The compression and decompression volumes do not flow through the injection valve. Consequently, the service life of the (high-pressure) injection valve of the sample injector is only limited by the unavoidable abrasion between the rotor and the stator and, if applicable, the abrasive effect, for example, of dirt particles or sample material.

As used herein, whether in the above description or the following claims, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The above described preferred embodiments are intended to illustrate the principles of the invention, but not to limit the scope of the invention. Various other embodiments and modifications to these preferred embodiments may be made by those skilled in the art without departing from the scope of the present invention.

The invention claimed is:

1. A sample injector for liquid chromatography, the sample injector including:
   (a) an injection valve having a waste port, first and second sample loop ports, and first and second high-pressure ports, the first high-pressure port adapted to be connected to a pump and the second high-pressure port adapted to be connected to a chromatography column;
   (b) a sample loop having (i) a first sample loop section operatively connected between the first sample loop port and a pump volume of a sample conveying device, (ii) a second sample loop section operatively connected between the second sample loop port and the pump volume of the sample conveying device, and (iii) an intake arrangement associated with the second sample loop section operable to selectively provide an opening in the second sample loop section to facilitate the intake of a sample fluid into a volume of the second sample loop section;
   (c) a control unit configured to (i) control the injection valve through a sample injection sequence, (ii) control the injection valve through a post sample injection sequence, or (iii) control the injection valve through both the injection sequence and the post sample injection sequence;
   (d) wherein in the sample injection sequence the control unit is configured to (i) place the injection valve in a LOAD position in which the first and second high-pressure ports are connected to one another and isolated from the sample loop, and the second sample loop port is operatively connected to the waste port, and to (ii) after intake of the sample fluid into the volume of the second sample loop section, place the injection valve in a PRESSURE COMPENSATION position in which the first and second sample loop ports are closed so as to facilitate pressurization of the sample loop by the sample conveying device to essentially the operating pressure of the pump, and to (iii) after pressurization of the sample loop, place the injection valve in an INJECT position in which the first high-pressure port is operatively connected to the first sample loop port and the second high-pressure port is operatively connected to the second sample loop port so as to facilitate passage of the sample fluid in the second sample loop section into the second sample loop port toward the second high-pressure port; and
   (e) wherein in the post sample injection sequence the control unit is configured to (i) move the injection valve from the INJECT position to the PRESSURE COMPENSATION position so as to facilitate reduction of the pressure in the sample loop to essentially ambient pressure by operation of the sample conveying device, and to (ii) move the injection valve from the PRESSURE COMPENSATION position to the LOAD position after the pressure in the sample loop is reduced.

2. The sample injector of claim 1 wherein the first and second high-pressure ports are connected when the injection valve is in the PRESSURE COMPENSATION position.

3. The sample injector of claim 2 wherein the injection valve includes:
   (a) a rotor;
   (b) a stator having a face that cooperates with a face of the rotor, and in which is formed the first and second high-pressure ports, the first and second sample ports, and the waste port; and
   (c) at least three grooves formed in the face of the rotor in position to place the first and second high-pressure ports, the first and second sample loop ports, and the waste port in their respective conditions in the LOAD, INJECTION, and PRESSURE COMPENSATION positions of the injection valve as a function of the rotational position of the rotor relative to the stator, and wherein the at least three grooves include a first groove that connects the first and second high-pressure ports when the injection valve is in the LOAD position, the first groove being sufficiently long so that it still connects the first and second high-pressure ports once the rotor is turned to the PRESSURE COMPENSATION position for the injection valve.

4. The sample injector of claim 1 wherein the sample conveying device is configured to generate pressures greater than 1000 bar.

5. The sample injector of claim 1 wherein the sample conveying device includes:
   (a) a device body having a cavity formed therein;
   (b) a movable element mounted in the device body, with the pump volume of the sample conveying device defined between the cavity of the device body and the moveable element, the moveable element being movable with respect to the device body to vary the pump volume;
   (c) a drive operatively connected to move the movable element with respect to the device body; and
   (d) wherein the control unit is configured to control the drive of the sample conveying device.

6. The sample injector of claim 5 wherein the control unit is configured to (i) once the injection valve is in the PRESSURE COMPENSATION position after having been switched from the INJECT position, control the drive of the sample conveying device to move the movable element by a respective predetermined distance to increase the pump volume sufficiently to reduce the pressure in the sample loop to essentially the ambient pressure, and to (ii) once the injection valve is in the PRESSURE COMPENSATION position after having been switched from the LOAD position, control the drive of the sample conveying device to move the movable element by a respective predetermined distance to decrease the pump volume sufficiently to increase the pressure in the sample loop to essentially the operating pressure of the pump.

7. The sample injector of claim 5 wherein the control unit controls the movement of the movable element of the sample conveying device in a given sample injection sequence or a given post sample injection sequence at least in part based on a pressure drop detected upon switching the injection valve from the PRESSURE COMPENSATION position to the INJECT position in a previous sample injection sequence.

8. The sample injector of claim 5 further including a sensor device configured to measure the force exerted upon the movable element by the drive of the conveying device, wherein a signal of said sensor device is fed to the control unit, and wherein the control unit is configured to determine the pressure of the fluid in at least one of the sample loop or the pump volume of the sample conveying device from the received signal at least while the injection valve is in the PRESSURE COMPENSATION position.

9. The sample injector according to claim 1 further including a pressure sensor configured to measure the pressure of the fluid in at least one of the sample loop or the pump volume of the sample conveying device at least while the injection valve is in the PRESSURE COMPENSATION position.

10. The sample injector of claim 9 wherein the signal of the pressure sensor is fed to the control unit and the control unit is configured to (i) in the sample injection sequence, compare the pressure indicated by the pressure sensor signal with a nominal high-pressure value and control the sample conveying device and the injection valve in such a way that the pressure indicated by the pressure sensor signal reaches the nominal high-pressure value before the injection valve is changed over from the PRESSURE COMPENSATION position to the INJECT position in the injection sequence, or to (ii) in the post sample injection sequence, compare the pressure indicated by the pressure sensor signal with a nominal low-pressure value and control the sample conveying device and the injection valve in such a way that the pressure indicated by the pressure sensor signal reaches the nominal low-pressure value before the injection valve is changed over from the PRESSURE COMPENSATION position to the LOAD position in the post sample injection sequence.

11. The sample injector of claim 1 wherein the control unit controls the sample conveying device based at least in part on compression properties of a fluid to be conveyed through the sample injector.

12. A liquid chromatography system including:
   (a) a high-pressure pump;
   (b) a chromatography column;
   (c) an injection valve having a waste port, first and second sample loop ports, a first high pressure port operatively connected to the high-pressure pump, and a second high-pressure port operatively connected to the chromatography column;
   (d) a sample loop having (i) a first sample loop section operatively connected between the first sample loop port and a pump volume of a sample conveying device, (ii) a second sample loop section operatively connected between the second sample loop port and the pump volume of the sample conveying device, and (iii) an intake arrangement associated with the second sample loop section operable to selectively provide an opening in the second sample loop section to facilitate the intake of a sample fluid into a volume of the second sample loop section;
   (e) a control unit configured to (i) control the injection valve through a sample injection sequence, (ii) control the injection valve through a post sample injection sequence, or (iii) control the injection valve through both the injection sequence and the post sample injection sequence;
   (f) wherein in the sample injection sequence the control unit is configured to (i) place the injection valve in a LOAD position in which the first and second high-pressure ports are connected to one another and isolated from the sample loop, and the second sample loop port is operatively connected to the waste port, and to (ii) after intake of the sample fluid into the volume of the second sample loop section, place the injection valve in a PRESSURE COMPENSATION position in which the first and second sample loop ports are closed so as to facilitate pressurization of the sample loop by the sample conveying device to essentially the operating pressure of the pump, and to (iii) after pressurization of the sample loop, place the injection valve in an INJECT position in which the first high-pressure port is operatively connected to the first sample loop port and the second high-pressure port is operatively connected to the second sample loop port so as to facilitate passage of the sample fluid in the second sample loop section into the second sample loop port toward the second high-pressure port; and (g) wherein in the post sample injection sequence the control unit is configured to (i) move the injection valve from the INJECT position to the PRESSURE COMPENSATION position so as to facilitate reduction of the pressure in the sample loop to essentially ambient pressure by operation of the sample conveying device, and to (ii) move the injection valve from the PRESSURE COMPENSATION position to the LOAD position after the pressure in the sample loop is reduced.

13. The sample injector of claim 12 wherein the injection valve includes:
(a) a rotor;
(b) a stator having a face that cooperates with a face of the rotor, and in which is formed the first and second high-pressure ports, the first and second sample ports, and the waste port; and
(c) at least three grooves formed in the face of the rotor in position to place the first and second high-pressure ports, the first and second sample loop ports, and the waste port in their respective conditions in the LOAD, INJECTION, and PRESSURE COMPENSATION positions of the injection valve as a function of the rotational position of the rotor relative to the stator, and wherein the at least three grooves include a first groove that connects the first and second high-pressure ports when the injection valve is in the LOAD position, the first groove being sufficiently long so that it still connects the first and second high-pressure ports once the rotor is turned to the PRESSURE COMPENSATION position for the injection valve.

14. The sample injector of claim 12 wherein the sample conveying device includes:
(a) a device body having a cavity formed therein;
(b) a movable element mounted in the device body with the pump volume of the sample conveying device defined between the cavity of the device body and the moveable element, the moveable element being movable with respect to the device body to vary the pump volume of the sample conveying device;
(c) a drive operatively connected to move the movable element with respect to the device body; and
(d) wherein the control unit is configured to control the drive of the sample conveying device.

15. The sample injector according to claim 12 further including a pressure sensor configured to measure the pressure of the fluid in at least one of the sample loop or the pump volume of the sample conveying device at least while the injection valve is in the PRESSURE COMPENSATION position.

* * * * *